United States Patent
Wrenn, Jr.

(10) Patent No.: US 6,174,873 B1
(45) Date of Patent: Jan. 16, 2001

(54) ORAL ADMINISTRATION OF ADENOSINE ANALOGS

(75) Inventor: Simeon M. Wrenn, Jr., Danville, CA (US)

(73) Assignee: SuperGen, Inc., San Ramon, CA (US)

( * ) Notice: Under 35 U.S.C. 154(b), the term of this patent shall be extended for 0 days.

(21) Appl. No.: 09/185,909

(22) Filed: Nov. 4, 1998

(51) Int. Cl.$^7$ .................................................. A61K 31/70
(52) U.S. Cl. ............................. 514/45; 514/46; 514/821; 514/885; 514/908; 514/959; 514/963; 514/964; 424/457; 424/458; 424/460; 424/463; 424/464; 424/469; 424/470
(58) Field of Search ................................ 514/45, 46, 963, 514/964, 821, 908, 885, 959; 424/457, 458, 463, 464, 469, 470, 460

(56) References Cited

U.S. PATENT DOCUMENTS

| | | | |
|---|---|---|---|
| 3,923,785 | 12/1975 | Ryder et al. | 260/211.5 R |
| 3,952,741 | * 4/1976 | Baker | 424/405 |
| 4,163,839 | 8/1979 | Umezama et al. | 536/24 |
| 4,713,372 | 12/1987 | Schaumberg et al. | 514/45 |
| 4,912,092 | 3/1990 | Gruber | 514/45 |
| 5,000,886 | 3/1991 | Lawter et al. | 264/4.3 |
| 5,087,618 | 2/1992 | Bodor | 514/45 |
| 5,132,291 | 7/1992 | Gruber | 514/43 |
| 5,143,661 | 9/1992 | Lawter et al. | 264/4.3 |
| 5,310,732 | 5/1994 | Carson et al. | 514/46 |
| 5,366,960 | 11/1994 | Gallagher | 514/43 |
| 5,459,256 | 10/1995 | Marquez et al. | 536/27.14 |
| 5,518,730 | 5/1996 | Fuisz | 424/426 |
| 5,521,162 | 5/1996 | Jarvi et al. | 514/46 |
| 5,633,274 | * 5/1997 | Halperin et al. | 514/405 |
| 5,635,156 | 6/1997 | Ildstad | 424/1.49 |
| 5,654,287 | 8/1997 | Prakash et al. | 514/49 |
| 5,663,155 | 9/1997 | McCaffrey et al. | 514/45 |
| 5,679,648 | 10/1997 | McCaffrey et al. | 514/46 |

OTHER PUBLICATIONS (Abstract) Gjedde SB, et al.; Chronic Lymphatic Leukemia. Peroral Cladribine as Primary Treatment; Ugeskr Laeger Nov. 4, 1996; 158(45):6432–4.

(Abstract) Juliusson G, et al.; Oral Cladribine as Primary Therapy for Patients with B–Cell Chronic Lymphocytic Leukemia; J Clin Oncol Jul.;, 1996 14(7):2160–6.

Dion et al. Ann N.Y. Acad. Sci. vol. 284, p. 21 (1997).*

* cited by examiner

Primary Examiner—James O. Wilson
(74) Attorney, Agent, or Firm—David J. Weitz; Wilson Sonsini; Goodrich & Rosati

(57) ABSTRACT

Disclosed are compositions including an adenosine analog, wherein the composition comprises a dosage form suitable for oral (co)administration. Also disclosed are compositions including adenosine analogs, wherein the composition is in a dosage form including a pill, capsule, lozenge, or tablet, and compositions including adenosine analogs, wherein the composition is in a dosage form comprising a liquid. Additionally disclosed are methods of administering the inventive composition, and kits including the inventive compositions.

11 Claims, No Drawings

ORAL ADMINISTRATION OF ADENOSINE ANALOGS

BACKGROUND OF THE INVENTION

1. Field of the Invention

This invention relates to compositions comprising an adenosine analog. More particularly, the invention relates to compositions comprising an adenosine analog, wherein the composition comprises a dosage form suitable for oral (co)administration.

2. Description of Related Art

Certain adenosine analogs have been found to have very useful clinical pharmacological benefits. These include, but are not limited to, 2'-deoxycoformycin (also referred to as dCF, pentostatin, or NIPENT®), an inhibitor of adenosine deaminase; fludarabine monophosphate (FLU), a fluorinated analogue of adenine that is relatively resistant to adenosine-deaminase and 2-chloro-2'-deoxyadenosine (also known as cladribine or 2CDA) a drug also resistant to adenosine deaminase through introduction of a chlorine at the 2 carbon. Other adenosine analogs that have useful activity include deoxyadenosines generally, including 2'-deoxyadenosine, 3'-deoxyadenosine, and dideoxyadenosine.

In humans, these compounds are assumed to act through a number of adenosine related pathways, particularly the adenosine deaminase (ADA) pathway. A genetic deficiency of ADA may cause severe combined immunodeficiency. Dighiero, G., "Adverse and beneficial immunological effects of purine nucleoside analogues," *Hematol Cell Ther*, 38:575–581 (1996). This document, and all others cited herein, are incorporated by reference as if reproduced fully herein.

While the exact nature of the ADA pathway intervention seems unclear, it may be that analogs of adenosine resistant to cellular deamination might mimic the ADA-deficient state. Lack of ADA seems to lead to a build up of deoxyadenosine and adenosine triphosphate in the cell, thus fatally accelerating DNA strand breaks in the cell. Under normal conditions, cells are continuously breaking and rejoining DNA. When this physiological process is accelerated by the effect of excess adenosine triphosphate, it leads to consumption of NAD for poly-ADP-ribose synthesis. This polymer is produced from nicotinamide adenosine dinucleotides (NAD) in a reaction catalyzed by the chromatin-associated poly(ADP-ribose) synthetase, leading to a depletion of the NAD content of the cell. This depletion induces a profound alteration of cellular reducing power, because of lethal ADP and ATP depletion.

The result is programmed cell death through activation of a Ca++, Mg++, dependent endonuclease. Hence, it appears that nucleoside analogs according to the invention can act on cells, with preferential lymphocytic activity, via an apoptotic process. The fact that supplementation of a cell medium with the NAD precursor of nicotinamide or 3-aminobenzamide, an inhibitor of poly (ADP-ribose) synthetase, prevented NAD depletion and reduces 2CDA toxicity, tends to support this hypothesis.

The various adenosine analogs affect the ADA pathway in different manners. DCF, for example, has been shown to be an quasi-irreversible inhibitor of ADA. By favoring the predominance of deoxycytidine kinase (DCK) over the dephosphorylating enzyme 5-nucleotidase in lymphocytes it induces a preferential accumulation of deoxyadenosine-5'-triphosphate (dATP). By comparison, FLU and 2CDA are rather resistant to the enzyme. Both drugs are initially phosphorylated by DCK and contribute to the accumulation of cellular adenosine triphosphate surrogates. As noted above, the accumulation of adenosine triphosphate, whether by the presumed DCF mechanism, or the FLU or 2CDA mechanism, promotes the apoptotic death of the cell.

Additional discussion of possible mechanisms of various adenosine analogs may be found in C. Dearden, et al., "Deoxycoformycin in the treatment of mature T-cell leukemias", *Brit J. of Can.*, 64(5):903–906 (November 1991); J. Seymour et al., "Response duration and recovery of CD4+ lymphocytes following deoxycoformycin in interferon-α-resistant hairy cell leukemia: 7-year follow-up", *Leukemia*, 11, 42–47 (1997); J. Johnston et al., "Induction of Apoptosis in CD4+ Prolymphocytic Leukemia by Deoxyadenosine and 2'-Deoxycoformycin", *Leukemia Research*, 16:8, 781–788 (1992); I. Fabian et al., "The Effect of Deoxycoformycin on Bone Marrow Cells Treated with Adenosine and Deoxyadenosine and Hemopoietic Growth Factors", *Human Immunology*, 21, 81–87 (1988); E. Copelan et al., "Pharmacologic Marrow Purging in Murine T Cell Leukemia", *Blood*, 71(6):1656–1661 (June 1988); W. Sheridan et al., "Preclinical studies on deoxycoformycin and deoxyadenosine as pharmacologic T cell purging tools" *Bone Marrow Trans.* 4:511–517 (1989); S. Sandhu et al., "Adenosine deaminase inhibitors attenuate ischemic injury and preserve energy balance in isolated guinea pig heart", 265(4):1249–1256 (October 1993); D. Saito et al., "Effect of adenosine deaminase inhibitors on myocardial reactive hyperaemia following brief coronary occlusions", *Cardiovascular Research*, 19, 578–583 (1985); G. Cristalli et al., "Adenosine Deaminase Inhibitors: Synthesis and Structure—Activity Relationships of Imidazole Analogues of erythro-9-(2-Hydroxy-3-nonyl)adenine", *J. Med. Chem.* 34:1187–1192 (1991); G. Cristalli et al., "Adenosine Deaminase Inhibitors. Synthesis and Biological Activity of Deaza Analogues of erythro-9-(2-Hydroxy-3-nonyl)adenine", *J. Med. Chem.*, 31:390–393 (1988); R. Jackson et al., "The Biochemical Pharmacology of (2'-R)-Chloropentostatin, a Novel Inhibitor of Adenosine Deaminase", *Advances in Enzyme Regulation*, 25:125–139; C. Vargeese, et al., "Adenosine Deaminase Inhibitors. Synthesis and Biological Evaluation of Putative Metabolites of (+)-erythro-9-(2S-Hydroxy-3R-nonyl)adenine", *J. Med. Chem.* 37:3844–3849 (1994); G. Wolberg et al., "Effects of Adenosine Deaminase Inhibitors on Lymphocyte-mediated Cytolysis", *Annals of the New York Academy of Sciences*, 451:215–226 (1985); G. Harriman et al., "Adenosine Deaminase Inhibitors. Synthesis and Biological Evaluation of 4-Amino-1-(2(S)-hydroxy-3(R)-nonyl)-1H-imidazo[4,5-c]pyridine (3-Deaza-(+)-EHNA) and Certain C1' Derivatives", *J. Med. Chem.* 37:305–308 (1994); I. Antonini et al., "Adenosine Deaminase Inhibitors. Synthesis of Deaza Analogues of erythro-9-(2-Hydroxy-3-nonyl)adenine" *J. Med. Chem.* 27:274–278 (1984); G. Cristalli et al., "Adenosine Deaminase Inhibitors: Synthesis and Structure—Activity Relationships of 2-Hydroxy-3-nonyl Derivatives of Azoles", *J. Med. Chem.*, 37:201–205 (1994); and H. Showalter et al., "Adenosine Deaminase Inhibitors. Synthesis and Biological Evaluation of (±)-3,6,7,8-Tetrahydro-3-[2-hydroxyethoxy)methyl]imidazo[4,5,-d][1,3]diazepin-8-ol and Some Selected C-5 Homologues of Pentostatin", *J. Med. Chem.* 26:1478–1482 (1983).

A problem with administering these adenosine analogs is their dosage form. Currently, these analogs are available only in an intravenous (IV) dosage form. While this dosage form is customary, especially for use in oncology indications, it is limiting in a variety of ways. For example, IV dosing is expensive. It requires a highly trained medical professional to administer the IV dose. The dosing involves expensive equipment and materials. Additionally, IV dosing presents increased possibilities of infection, through use of contaminated equipment or accidental contamination, for example. This is a special concern in health care settings where increased incidences of antibiotic resistant bacteria are being noted.

A seemingly natural solution to the IV dosage problem is the development of an oral dosage form. Such a dosage form alleviates most, if not all, of the above-mentioned problems associated with IV or other parenteral dosage forms. However, the art recognized serious problems with the development of an oral dosage form. Chief among these is that adenosine analogs have been known for years to be susceptible to acid-catalyzed glycosidic cleavage. Therefore, one of skill in the art would expect that an orally administered adenosine analog would be cleaved in the stomach, and rendered inactive.

For example, investigators studying 2'-deoxycoformycin, an adenosine analog, have not considered oral administration of the drug worth studying because of its known acid lability. Marvin M. Chassin et al., Enzyme Inhibition Titration Assay for 2'-deoxycoformycin and its Application to the Study of the Relationship Between Drug Concentration and Tissue Adenosine Deaminase in Dogs and Rats, Biochemical Pharmacology 28:1849–1855 (1979). Likewise, other researchers have reported on the acid lability of 2'-deoxycoformycin. L. A. al-Razzak et al., Chemical Stability of Pentostatin (NSC-218321). a Cytotoxic and Immunosuppressant Agent, Pharm. Res. 7:452–460 (1990).

Other adenosine analogs may be expected to have similar acid lability characteristics. A. Tarasiuk et al., Stability of 2-chloro-2'-deoxyadenosine at Various pH and Temperature, Arch. Immunol. Ther. Exp. (Warsz) 42:13–15 (1994); T. Ono, 2'-Fluoro Modified Nucleic Acids: Polymerase-directed Synthesis, Properties and Stability to Analysis by Matrix-Assisted Laser Desorption/Ionization Mass Spectrometry, Nucleic Acids Res. 25:4581–4588 (1997). Therefore, the art has taught away from orally dosing adenosine analogs, despite its usefulness. Accordingly, the need remains for compositions, methods and kits for oral dosing of adenosine analogs.

SUMMARY OF THE INVENTION

In one aspect, the invention relates to a composition comprising an adenosine analog, wherein the composition comprises a dosage form suitable for oral (co) administration. In another aspect, the invention relates to a composition comprising adenosine analogs, wherein the composition is in a dosage form comprising a pill, capsule, lozenge, or tablet. In still another aspect, the invention relates to a composition comprising adenosine analogs, wherein the composition is in a dosage form comprising a liquid.

DETAILED DESCRIPTION OF THE INVENTION

In an aspect, the invention relates to a composition comprising an adenosine analog, wherein the composition comprises a dosage form suitable for oral (co) administration. In another aspect, the invention relates to the composition wherein the composition comprises a controlled release composition. In still another aspect, the invention relates to the composition wherein the composition comprises a dosage form that reduces acid lability of the adenosine analog, thereby enhancing the bioavailability the adenosine analog. In yet another aspect, the invention relates to the composition wherein the composition comprises a controlled release composition.

In another aspect, the invention relates to the composition wherein the composition is in a dosage form that comprises a physical system or a chemical system. In still another aspect, the invention relates to the composition wherein the physical system comprises reservoir systems with rate-controlling membranes; reservoir systems without rate-controlling membranes; monolithic systems; materials physically dispersed in non-porous, polymeric, or elastomeric matrices; laminated structures; osmotic pumps; or adsorption onto ion-exchange resins. In yet another aspect, the invention relates to the composition wherein the chemical system comprises polymer matrices that are erodible chemically or biologically.

In a further aspect, the invention relates to the composition wherein the composition comprises a rate-preprogrammed drug delivery system, an activation-modulated drug delivery system, a feedback-regulated drug delivery system, or a site-targeting drug delivery system. In another aspect, the invention relates to the composition wherein the composition is in a dosage form comprising SODAS, INDAS, IPDAS, MODAS, EFVAS, PRODAS, or DUREDAS. In yet another aspect, the invention relates to the composition wherein the composition is in a dosage form suitable for delivery orally, mucosally, or nasally.

In still another aspect, the invention relates to the composition wherein the composition comprises an enteric coating. In a further aspect, the invention relates to the composition wherein the enteric coating comprises hydroxypropylmethylcellulose phthalate, methacrylic acid-methacrylic acid ester copolymer, polyvinyl acetate-phthalate and cellulose acetate phthalate. In still another aspect, the invention relates to the composition wherein the composition comprises a solid dispersion. In yet another aspect, the invention relates to the composition wherein the solid dispersion comprises a water soluble or a water insoluble carrier. In another aspect, the invention relates to the composition wherein the water soluble or water insoluble carrier comprises polyethylene glycol, polyvinylpyrrolidone, hydroxypropylmethyl—cellulose, phosphatidylcholine, polyoxyethylene hydrogenated castor oil, hydroxypropylmethylcellulose phthalate, carboxymethylethylcellulose, or hydroxypropylmethylcellulose, ethyl cellulose, or stearic acid In still another aspect, the invention relates to the composition wherein the composition is in a dosage form comprising a complex between an ion exchange resin and the adenosine analog. In another aspect, the invention relates to the composition wherein the composition is in a dosage form comprising injectable micro spheres. In a further aspect, the invention relates to the composition wherein the composition is in a dosage form comprising a pill, capsule, liquid, lozenge, or tablet.

In another aspect, the invention relates to the composition wherein liquid dosage forms, controlled release dosage forms, or liposomal dosage forms are excluded. In still another aspect, the invention relates to the composition wherein the excluded controlled release dosage forms comprise a physical system or a chemical system. In yet another aspect, the invention relates to the composition wherein the physical system comprises reservoir systems with rate-controlling membranes; reservoir systems without rate-controlling membranes; monolithic systems; materials physically dispersed in non-porous, polymeric, or elastomeric matrices; laminated structures; osmotic pumps; or adsorption onto ion-exchange resins. In yet another aspect, the invention relates to the composition wherein the chemical system comprises polymer matrices that are erodible chemically or biologically. In still another aspect, the invention relates to the composition wherein the excluded controlled release dosage forms comprise a rate-preprogrammed drug delivery system, an activation-modulated drug delivery system, a feedback-regulated drug delivery system, or a site-targeting drug delivery system. In another aspect, the invention relates to the composition wherein the excluded controlled release dosage forms comprise an enteric coating. In still another aspect, the invention relates to the composition wherein the excluded controlled release dosage forms comprise a solid dispersion. In another aspect, the invention relates to the composition wherein the solid dispersion comprises a water soluble or a water insoluble carrier.

In another aspect, the invention relates to the composition wherein the adenosine analog is present in an amount effective to treat hematological malignancies, solid tumors sensitive to adenosine analogs or adenosine deaminase inhibitors, ischemia, CD4+ T cell mediated diseases, autoimmune diseases mediated by adenosine or adenosine deaminase, inflammatory diseases mediated by adenosine or adenosine deaminase, stroke, myocardial infarction, and ventricular arrhythmia. In yet another aspect, the invention relates to the composition wherein the adenosine analog is present in an amount effective to treat leukemia. In still another aspect, the invention relates to the composition wherein the leukemia comprises hairy cell leukemia, and chronic lymphocytic leukemia, chronic T-cell lymphoma, acute myelogenous lymphoma, hairy cell leukemia, or chronic lymphocytic leukemia.

In an aspect, the invention relates to compositions comprising adenosine analogs, wherein the composition is in a dosage form comprising a pill, capsule, lozenge, or tablet. In another aspect, the invention relates to the composition wherein the composition is in a dosage form comprising a liquid.

In another aspect, the invention relates to methods of administering compositions comprising adenosine analogs to a host in need thereof, comprising providing the composition described above, and administering that composition to the host. In yet another aspect, the invention relates to the method wherein the composition comprises a controlled release composition. In still another aspect, the invention relates to the method wherein the composition comprises a dosage form that reduces acid lability of the adenosine analog, thereby enhancing the bioavailability of the adenosine analog. In yet another aspect, the invention relates to the method wherein the composition comprises a controlled release composition.

In another aspect, the invention relates to the method wherein the composition is in a dosage form that comprises a physical system or a chemical system. In still another aspect, the invention relates to the method wherein the physical system comprises reservoir systems with rate-controlling membranes; reservoir systems without rate-controlling membranes; monolithic systems; materials physically dispersed in non-porous, polymeric, or elastomeric matrices; laminated structures; osmotic pumps; or absorption onto ion-exchange resins. In yet another aspect, the invention relates to the method wherein the composition comprises a rate-preprogrammed drug delivery system, an activation-modulated drug delivery system, a feedback-regulated drug delivery system, or a site-targeting drug delivery system.

In yet another aspect, the invention relates to the method wherein the composition is in a dosage form comprising SODAS, INDAS, IPDAS, MODAS, EFVAS, PRODAS, or DUREDAS. In another aspect, the invention relates to the method wherein the composition is in a dosage form suitable for delivery orally, mucosally, or nasally. In still another aspect, the invention relates to the method wherein the composition comprises an enteric coating. In yet another aspect, the invention relates to the method wherein the composition comprises a solid dispersion. In another aspect, the invention relates to the method wherein the solid dispersion comprises a water soluble or a water insoluble carrier. In another aspect, the invention relates to the method wherein the composition is in a dosage form comprising a complex between an ion exchange resin and the adenosine analog. In still another aspect, the invention relates to the method wherein the composition is in a dosage form comprising injectable micro spheres.

In an aspect, the invention relates to kits comprising the composition described above.

The invention will now be discussed in more detail. The inventors have unexpectedly discovered that, despite the demonstrated acid lability of adenosine analogs, it is possible to achieve bioavailability of the analogs using dosage forms suitable for oral (co)administration. In fact, it is surprisingly possible to achieve effects using an oral dosage form that are reasonably close to those achieved using an IV dosage form. These unexpected results are expanded below.

The adenosine analogs included in the invention include structural analogs of adenosine that are physiologically active. These include, but are not limited to, 2'-deoxycoformycin (also referred to as DCF, pentostatin, or NIPENT®), an inhibitor of adenosine deaminase; fludarabine monophosphate (FLU), a fluorinated analogue of adenine that is relatively resistant to adenosine-deaminase and 2-chloro-2'-deoxyadenosine (also known as cladribine or 2CDA) a drug also resistant to adenosine deaminase through introduction of a chlorine at the 2 carbon. Other adenosine analogs that have useful activity include deoxyadenosines generally, including 2'-deoxyadenosine, 3'-deoxyadenosine, and dideoxyadenosine. Also included in the class of adenosine analogs are prodrugs of the analogs. Such prodrugs includes phosphates, esters, and amides of the adenosine analogs.

In some cases, it may be appropriate to administer the adenosine analogs in the form of their therapeutically acceptable salts. These salts may be prepared in the conventional manner.

Salt formers that may, for example, be used are conventional anions or salts thereof that are physiologically acceptable in the salt form. Examples thereof are: amino acids such as tyrosine or asparagine, sulfates, phosphates, carboxylic acids, tosylates, nitrates, acetates, and long chain fatty acid derivatives of these.

Should the adenosine analogs be used in the form of their salts, the salt former may also be used in excess, i.e. in an amount greater than equimolar.

Various dosage forms of adenosine analogs may be used in the practice of the invention. For example, the adenosine analogs may be mixed with a pharmacologically acceptable liquid and swallowed. The adenosine analogs also may be compounded into tablets, capsules, pills, lozenges, etc. using conventional compounding techniques.

In one embodiment, the adenosine analogs may be administered with various agents to reduce acid concentration in the stomach. This reduces acid lability and allows for enhanced concentrations of adenosine analog for enhanced gastric and/or intestinal absorption. For example, the adenosine analog may be coadministered with an H2 inhibitor such as cimetidine, an acid neutralizer such as calcium carbonate, or a proton pump inhibitor.

Furthermore, the adenosine analogs may be (co) administered using a dosage form that reduces the effect of acid lability on their bioavailability. (Co)administration within the context of this invention may be taken to mean administration, coadministration, or both. Coadministration in the context of this invention may be defined to mean the administration of more than one therapeutic in the course of a coordinated treatment to achieve an improved clinical outcome. Such coadministration may also be coextensive, that is, occurring during overlapping periods of time.

For example, in a preferable embodiment, the adenosine analogs may be administered using controlled release dosage forms. Controlled release within the scope of this invention can be taken to mean any one of a number of extended release dosage forms.

The following terms may be considered to be substantially equivalent to controlled release, for the purposes of the present invention: continuous release, controlled release, delayed release, depot, gradual release, long-term release, programmed release, prolonged release, proportionate release, protracted release, repository, retard, slow release, spaced release, sustained release, time coat, timed release, delayed action, extended action, layered-time action, long acting, prolonged action, repeated action, slowing acting, sustained action, sustained-action medications, and extended release. Further discussions of these terms may be found in Lesczek Krowczynski, *Extended-Release Dosage Forms*, 1987 (CRC Press, Inc.).

The various controlled release technologies cover a very broad spectrum of drug dosage forms. Controlled release technologies include, but are not limited to physical systems and chemical systems.

Physical systems include, but not limited to, reservoir systems with rate-controlling membranes, such as microencapsulation, macroencapsulation, and membrane systems; reservoir systems without rate-controlling membranes, such as hollow fibers, ultra microporous cellulose triacetate, and porous polymeric substrates and foams; monolithic systems, including those systems physically dissolved in non-porous, polymeric, or elastomeric matrices (e.g., non-erodible, erodible, environmental agent ingression, and degradable), and materials physically dispersed in non-porous, polymeric, or elastomeric matrices (e.g., non-erodible, erodible, environmental agent ingression, and degradable); laminated structures, including reservoir layers chemically similar or dissimilar to outer control layers; and other physical methods, such as osmotic pumps, or adsorption onto ion-exchange resins.

Chemical systems include, but are not limited to, chemical erosion of polymer matrices (e.g., heterogeneous, or homogeneous erosion), or biological erosion of a polymer matrix (e.g., heterogeneous, or homogeneous). Additional discussion of categories of systems for controlled release may be found in Agis F. Kydonieus, *Controlled Release Technologies: Methods, Theory and Applications*, 1980 (CRC Press, Inc.).

Controlled release drug delivery systems may also be categorized under their basic technology areas, including, but not limited to, rate-preprogrammed drug delivery systems, activation-modulated drug delivery systems, feedback-regulated drug delivery systems, and site-targeting drug delivery systems.

In rate-preprogrammed drug delivery systems, release of drug molecules from the delivery systems "preprogrammed" at specific rate profiles. This may be accomplished by system design, which controls the molecular diffusion of drug molecules in and/or across the barrier medium within or surrounding the delivery system. Fick's laws of diffusion are often followed.

In activation-modulated drug delivery systems, release of drug molecules from the delivery systems is activated by some physical, chemical or biochemical processes and/or facilitated by the energy supplied externally. The rate of drug release is then controlled by regulating the process applied, or energy input.

In feedback-regulated drug delivery systems, release of drug molecules from the delivery systems may be activated by a triggering event, such as a biochemical substance, in the body. The rate of drug release is then controlled by the concentration of triggering agent detected by a sensor in the feedback regulated mechanism.

In a site-targeting controlled-release drug delivery system, the drug delivery system targets the active molecule to a specific site or target tissue or cell. This may be accomplished, for example, by a conjugate including a site specific targeting moiety that leads the drug delivery system to the vicinity of a target tissue (or cell), a solubilizer that enables the drug delivery system to be transported to and preferentially taken up by a target tissue, and a drug moiety that is covalently bonded to the polymer backbone through a spacer and contains a cleavable group that can be cleaved only by a specific enzyme at the target tissue.

While a preferable mode of controlled release drug delivery will be oral, other modes of delivery of controlled release compositions according to this invention may be used. These include mucosal delivery, nasal delivery, ocular delivery, transdermal delivery, parenteral controlled release delivery, vaginal delivery, rectal delivery and intrauterine delivery. All of these dosage forms may be manufactured using conventional techniques, together with the techniques discussed herein.

There are a number of controlled release drug formulations that are developed preferably for oral administration. These include, but are not limited to, osmotic pressure-controlled gastrointestinal delivery systems; hydrodynamic pressure-controlled gastrointestinal delivery systems; membrane permeation-controlled gastrointestinal delivery systems, which include microporous membrane permeation-controlled gastrointestinal delivery devices; gastric fluid-resistant intestine targeted controlled-release gastrointestinal delivery devices; gel diffusion-controlled gastrointestinal delivery systems; and ion-exchange-controlled gastrointestinal delivery systems, which include cationic and anionic drugs. Additional information regarding controlled release drug delivery systems may be found in Yie W. Chien, *Novel Drug Delivery Systems*, 1992 (Marcel Dekker, Inc.). some of these formulations will now be discussed in more detail.

Enteric coatings may be applied to tablets to prevent the release of drugs in the stomach either to reduce the risk of unpleasant side effects or to maintain the stability of the drug which might otherwise be subject to degradation of expose to the gastric environment. Most polymers that are used for this purpose are polyacids that function by virtue of the fact that their solubility in aqueous medium is pH-dependent, and they require conditions with a pH higher then normally encountered in the stomach.

Enteric coatings may be used to coat a solid or liquid dosage form of adenosine analogs according to the invention. Enteric coatings promote the inventive adenosine analogs remaining physically incorporated in the dosage form for a specified period when exposed to gastric juice. Yet the enteric coatings are designed to disintegrate in intestinal fluid for ready absorption. Delay of the adenosine analogs' absorption is dependent on the rate of transfer through the gastrointestinal tract, and so the rate of gastric emptying is an important factor. Some investigators have reported that a multiple-unit type dosage form, such as granules, may be superior to a single-unit type. Therefore, in a preferable embodiment, the adenosine analogs according to the invention may be contained in an enterically coated multiple-unit dosage form. In a more preferable embodiment, the dosage form of the adenosine analogs according to the invention is prepared by spray-coating granules of an adenosine analog-enteric coating agent solid dispersion on an inert core material. These granules can result in prolonged absorption of the drug with good bioavailability.

Typical enteric coating agents include, but are not limited to, hyd roxypropylmethylcellulose phthalate, methacrylic acid-methacrylic acid ester copolymer, polyvinyl acetate-phthalate and cellulose acetate phthalate. Akihiko Hasegawa, Application of solid dispersions of Nifedipine with enteric coating agent to prepare a sustained-release dosage form, Chem. Pharm. Bull. 33: 1615–1619 (1985). Various enteric coating materials may be selected on the basis of testing to achieve an enteric coated dosage form designed ab initio to have a preferable combination of dissolution time, coating thicknesses and diametral crushing strength. S. C. Porter et al., The Properties of Enteric Tablet Coatings Made From Polyvinyl Acetate-phthalate and Cellulose acetate Phthalate, J. Pharm. Pharmacol. 22:42p (1970).

On occasion, the performance of an enteric coating may hinge on its permeability. S. C. Porter et al., The Permeability of Enteric Coatings and the Dissolution Rates of Coated Tablets, J. Pharm. Pharmacol. 34: 5–8 (1981). With such oral drug delivery systems, the drug release process may be initiated by diffusion of aqueous fluids across the enteric coating. Investigations have suggested osmotic driven/rupturing affects as important release mechanisms from enteric coated dosage forms. Roland Bodmeier et al., Mechanical Properties of Dry and Wet Cellulosic and Acrylic Films Prepared from Aqueous Colloidal Polymer Dispersions used in the Coating of Solid Dosage Forms, Pharmaceutical Research, 11: 882–888 (1994).

Another type of useful oral controlled release structure is a solid dispersion. A solid dispersion may be defined as a dispersion of one or more active ingredients in an inert carrier or matrix in the solid state prepared by the melting (fusion), solvent, or melting-solvent method. Akihiko Hasegawa, Super Saturation Mechanism of Drugs from Solid Dispersions with Enteric Coating Agents, Chem. Pharm. Bull. 36: 4941–4950 (1998). The solid dispersions may be also called solid-state dispersions. The term "coprecipitates" may also be used to refer to those preparations obtained by the solvent methods.

Solid dispersions may be used to improve the solubilities and/or dissolution rates of adenosine analogs according to the invention that may be poorly water-soluble. See generally Hiroshi Yuasa, et al., Application of the Solid Dispersion Method to the Controlled Release Medicine. III. Control of the Release Rate of Slightly Water-Soluble Medicine From Solid Dispersion Granules, Chem. Pharm. Bull. 41:397–399 (1993). The solid dispersion method was originally used to enhance the dissolution rate of slightly water-soluble medicines by dispersing the medicines into water-soluble carriers such as polyethylene glycol or polyvinylpyrrolidone, Hiroshi Yuasa, et al., Application of the Solid Dispersion Method to the Controlled Release of Medicine. IV. Precise Control of the Release Rate of a Water-Soluble Medicine by Using the Solid Dispersion Method Applying the Difference in the Molecular Weight of a Polymer, Chem. Pharm. Bull. 41:933–936 (1993).

The selection of the carrier may have an influence on the dissolution characteristics of the dispersed drug because the dissolution rate of a component from a surface may be affected by other components in a multiple component mixture. For example, a water-soluble carrier may result in a fast release of the drug from the matrix, or a poorly soluble or insoluble carrier may lead to a slower release of the drug from the matrix. The solubility of poorly water soluble adenosine analogs according to the invention may also be increased owing to some interaction with the carriers.

Examples of carriers useful in solid dispersions according to the invention include, but are not limited to, water-soluble polymers such as polyethylene glycol, polyvinylpyrrolidone, or hydroxypropylmethyl-cellulose. Akihiko Hasegawa, Application of Solid Dispersions of Nifedipine with Enteric Coating Agent to Prepare a Sustained-release Dosaae Form, Chem. Pharm. Bull. 33:1615–1619 (1985).

Alternate carriers include phosphatidyicholine. Makiko Fujii, et al., The Properties of Solid Dispersions of Indomethacin. Ketoprofen and Flurbiprofen in Phosphatidylcholine, Chem. Pharm. Bull. 36:2186–2192 (1988). Phosphatidylcholine is an amphoteric but water-insoluble lipid, which may improve the solubility of otherwise insoluble adenosine analogs in an amorphous state in phosphatidylcholine solid dispersions. See Makiko Fujii, et al., Dissolution of Bioavailability of Phenytoin in Solid Dispersion with Phosphatidylcholine, Chem. Pharm. Bull 36:4908–4913 (1988).

Other carriers include polyoxyethylene hydrogenated castor oil. Katsuhiko Yano, et al., In-Vitro Stability and In-Vivo Absorption Studies of Colloidal Particles Formed From a Solid Dispersion System, Chem. Pharm. Bull 44:2309–2313 (1996). Poorly water-soluble adenosine analogs according to the invention may be included in a solid dispersion system with an enteric polymer such as hydroxypropylmethylcellulose phthalate and carboxymethylethylcellulose, and a non-enteric polymer, hydroxypropylmethylcellulose. See Toshiya Kai, et al., Oral Absorption Improvement of Poorly Soluble Drug Using Soluble Dispersion Technique, Chem. Pharm. Bull. 44:568–571 (1996). Another solid dispersion dosage form includes incorporation of the drug of interest with ethyl cellulose and stearic acid in different ratios. Kousuke Nakano, et al., Oral Sustained-Release Cisplatin Preparations for Rats and Mice, J. Pharm. Pharmacol. 49:485–490 (1997).

There are various methods commonly known for preparing solid dispersions. These include, but are not limited to the melting method, the solvent method and the melting-solvent method.

In the melting method, the physical mixture of a drug in a water-soluble carrier is heated directly until it melts. The melted mixture is then cooled and solidified rapidly while rigorously stirred. The final solid mass is crushed, pulverized and sieved. Using this method a super saturation of a solute or drug in a system can often be obtained by quenching the melt rapidly from a high temperature. Under such conditions, the solute molecule may be arrested in solvent matrix by the instantaneous solidification process. A disadvantage is that many substances, either drugs or carriers, may decompose or evaporate during the fusion process at high temperatures. However, this evaporation problem may be avoided if the physical mixture is heated in a sealed container. Melting under a vacuum or blanket of an inert gas such as nitrogen may be employed to prevent oxidation of the drug or carrier.

The solvent method has been used in the preparation of solid solutions or mixed crystals of organic or inorganic compounds. Solvent method dispersions may be prepared by dissolving a physical mixture of two solid components in a common solvent, followed by evaporation of the solvent. The main advantage of the solvent method is that thermal decomposition of drugs or carriers may be prevented because of the low temperature required for the evaporation of organic solvents. However, some disadvantages associated with this method are the higher cost of preparation, the difficulty in completely removing liquid solvent, the possible adverse effect of its supposedly negligible amount of the solvent on the chemical stability of the drug.

Another method of producing solid dispersions is the melting-solvent method. It is possible to prepare solid dispersions by first dissolving a drug in a suitable liquid solvent and then incorporating the solution directly into a melt of polyethylene glycol, obtainable below 70 degrees, without removing the liquid solvent. The selected solvent or dissolved adenosine analogs may be selected such that the solution is not miscible with the melt of polyethylene glycol. The polymorphic form of the adenosine analogs may then be precipitated in the melt. Such a unique method possesses the advantages of both the melting and solvent methods. Win Loung Chiou, et al., Pharmaceutical Applications of Solid Dispersion Systems, J. Pharm. Sci. 60:1281–1301 (1971).

Another controlled release dosage form is a complex between an ion exchange resin and an adenosine analog according to the invention. Ion exchange resin-drug complexes have been used to formulate sustained-release products of acidic and basic drugs. In one preferable embodiment, a polymeric film coating is provided to the ion exchange resin-drug complex particles, making drug release from these particles diffusion controlled. See Y. Raghunathan et al., Sustained-released drug delivery system I: Coded ion-exchange resin systems for phenylpropanolamine and other drugs, J. Pharm. Sciences 70: 379–384 (1981).

Injectable micro spheres are another controlled release dosage form. Injectable micro spheres may be prepared by non-aqueous phase separation techniques, and spray-drying techniques. Micro spheres may be prepared using polylactic acid or copoly(lactic/glycolic acid). Shigeyuki Takada, Utilization of an Amorphous Form of a Water-Soluble GPIIb/IIIa Antagonist for Controlled Release From Biodegradable Micro spheres, Pharm. Res. 14:1146–1150 (1997), and ethyl cellulose, Yoshiyuki Koida, Studies on Dissolution Mechanism of Drugs from Ethyl Cellulose Microcapsules, Chem. Pharm. Bull. 35:1538–1545 (1987).

Other controlled release technologies that may be used in the practice of this invention are quite varied. They include SODAS (Spheroidal Oral Drug Absorption System), INDAS (Insoluble Drug Absorption System), IPDAS (Intestinal Protective Drug Absorption System), MODAS (Multiporous Oral Drug Absorption System), EFVAS (Effervescent Drug Absorption System), PRODAS (Programmable Oral Drug Absorption System), and DUREDAS (Dual Release Drug Absorption System) available from Elan Pharmaceutical Technologies, Dublin, Ireland. SODAS are multi particulate dosage forms utilizing controlled release beads. INDAS are a family of drug delivery technologies designed to increase the solubility of poorly soluble drugs. IPDAS are multi particulate tablet formation utilizing a combination of high density controlled release beads and an immediate release granulate. MODAS are controlled release single unit dosage forms. Each tablet consists of an inner core surrounded by a semipermeable multiparous membrane that controls the rate of drug release. EFVAS is an effervescent drug absorption system, PRODAS is a family of multi particulate formulations utilizing combinations of immediate release and controlled release mini-tablets. DUREDAS is a bilayer tablet formulation providing dual release rates within the one dosage form. Although these dosage forms are known to one of skill, certain of these dosage forms will now be discussed in more detail.

INDAS was developed specifically to improve the solubility and absorption characteristics of poorly water soluble drugs. Solubility and, in particular, dissolution within the fluids of the gastrointestinal tract is a key factor in determining the overall oral bioavailability of poorly water soluble drug. By enhancing solubility, one can increase the overall bioavailability of a drug with resulting reductions in dosage. INDAS takes the form of a high energy matrix tablet. In a preferred embodiment of the invention production involves including adenosine analogs in an amorphous form together with a combination of energy, excipients, and unique processing procedures.

Once included in the desirable physical form, the resultant high energy complex may be stabilized by an absorption process that utilizes a novel polymer cross-linked technology to prevent recrystallization. The combination of the change in the physical state of the adenosine analogs according to the invention coupled with the solubilizing characteristics of the excipients employed enhances the solubility of the adenosine analogs according to the invention. The resulting absorbed amorphous drug complex granulate may be formulated with a gel-forming erodable tablet system to promote substantially smooth and continuous absorption.

IPDAS is a multi-particulate tablet technology that may enhance the gastrointestinal tolerability of potential irritant and ulcerogenic drugs. Intestinal protection is facilitated by the multi-particulate nature of the IPDAS formulation which promotes dispersion of an irritant adenosine analog according to the invention throughout the gastrointestinal tract. Controlled release characteristics of the individual beads may avoid high concentration of drug being both released locally and absorbed systemically. The combination of both approaches serves to minimize the potential harm of the adenosine analog according to the invention with resultant benefits to patients.

IPDAS is composed of numerous high density controlled release beads. Each bead may be manufactured by a two step process that involves the initial production of a micromatrix with embedded adenosine analogs according to the invention and the subsequent coating of this micromatrix with polymer solutions that form a rate limiting semipermeable membrane in vivo. Once an IPDAS tablet is ingested, it may disintegrate and liberate the beads in the stomach. These beads may subsequently pass into the duodenum and along the gastrointestinal tract, preferably in a controlled and gradual manner, independent of the feeding state. Adenosine analog release occurs by diffusion process through the micromatrix and subsequently through the pores in the rate controlling semipermeable membrane. The release rate from the IPDAS tablet may be customized to deliver a drug-specific absorption profile associated with optimized clinical benefit. Should a fast onset of activity be necessary, immediate release granulate may be included in the tablet. The tablet may be broken prior to administration, without substantially compromising drug release, if a reduced dose is required for individual titration.

MODAS is a drug delivery system that may be used to control the absorption of water soluble adenosine analogs according to the invention. Physically MODAS is a non-disintegrating table formulation that manipulates drug release by a process of rate limiting diffusion by a semipermeable membrane formed in vivo. The diffusion process essentially dictates the rate of presentation of drug to the gastrointestinal fluids, such that the uptake into the body is controlled. Because of the minimal use of excipients, MODAS can readily accommodate small dosage size forms. Each MODAS tablet begins as a core containing active drug plus excipients. This core is coated with a solution of insoluble polymers and soluble excipients. Once the tablet is ingested, the fluid of the gastrointestinal tract may dissolve the soluble excipients in the outer coating leaving substantially the insoluble polymer. What results is a network of tiny, narrow channels connecting fluid from the gastrointestinal tract to the inner drug core of water soluble drug. This fluid passes through these channels, into the core, dissolving the drug, and the resultant solution of drug may diffuse out in a controlled manner. This may permit both controlled dissolution and absorption. An advantage of this system is that the drug releasing pores of the tablet are distributed over substantially the entire surface of the tablet. This facilitates uniform drug absorption and reduces aggressive unidirectional drug delivery. MODAS represents a very flexible dosage form in that both the inner core and the outer semipermeable membrane may be altered to suit the individual delivery requirements of a drug. In particular, the addition of excipients to the inner core may help to produce a micro environment within the tablet that facilitates more predictable release and absorption rates. The addition of an immediate release outer coating may allow for development of combination products.

Additionally, PRODAS may be used to deliver adenosine analogs according to the invention. PRODAS is a multi particulate drug delivery technology based on the production of controlled release mini tablets in the size range of 1.5 to 4 mm in diameter. The PRODAS technology is a hybrid of multi particulate and hydrophilic matrix tablet approaches, and may incorporate, in one dosage form, the benefits of both these drug delivery systems.

In its most basic form, PRODAS involves the direct compression of an immediate release granulate to produce individual mini tablets that contain adenosine analogs according to the invention. These mini tablets are subsequently incorporated into hard gels and capsules that represent the final dosage form. A more beneficial use of this technology is in the production of controlled release formulations. In this case, the incorporation of various polymer combinations within the granulate may delay the release rate of drugs from each of the individual mini tablets. These mini tablets may subsequently be coated with controlled release polymer solutions to provide additional delayed release properties. The additional coating may be necessary in the case of highly water soluble drugs or drugs that are perhaps gastroirritants where release can be delayed until the formulation reaches more distal regions of the gastrointestinal tract. One value of PRODAS technology lies in the inherent flexibility to formulation whereby combinations of mini tablets, each with different release rates, are incorporated into one dosage form. As well as potentially permitting controlled absorption over a specific period, this also may permit targeted delivery of drug to specific sites of absorption throughout the gastrointestinal tract. Combination products also may be possible using mini tablets formulated with different active ingredients.

DUREDAS is a bilayer tableting technology that may be used in the practice of the invention. DUREDAS was developed to provide for two different release rates, or dual release of a drug from one dosage form. The term bilayer refers to two separate direct compression events that take place during the tableting process. In a preferable embodiment, an immediate release granulate is first compressed, being followed by the addition of a controlled release element which is then compressed onto this initial tablet. This may give rise to the characteristic bilayer seen in the final dosage form.

The controlled release properties may be provided by a combination of hydrophilic polymers. In certain cases, a rapid release of the adenosine analogs according to the invention may be desirable in order to facilitate a fast onset of therapeutic affect. Hence one layer of the tablet may be formulated as an immediate release granulate. By contrast, the second layer of the tablet may release the drug in a controlled manner, preferably through the use of hydrophilic polymers. This controlled release may result from a combination of diffusion and erosion through the hydrophilic polymer matrix.

A further extension of DUREDAS technology is the production of controlled release combination dosage forms. In this instance, two different adenosine analogs according to the invention may be incorporated into the bilayer tablet and the release of drug from each layer controlled to maximize therapeutic affect of the combination.

One preferable example of coadministration is the combination of deoxyadenosines with pentostatin. This combination may operate synergistically, to obtain a differential effect over either of the therapeutic agents administered separately. It has been reported that pentostatin enhances the clinical anti-HIV activity of related adenosine analogs presumably due to prevention of degradation of the adenosine analogs by adenosine deaminase. G. S. Ahluwalia, et al., "Enhancement by 2'-deoxycoformycin of the 5"-Phosphorylation and Anti-Human immunodeficiency virus activity of 2'3'-dideoxyadenosine and 2'-beta-fluor-2', 3'-dideoxyadenosine", *Molec. Pharmacol.* 46:1002–1008 (1994).

Furthermore, the adenosine analogs may be administered or coadministered with conventional pharmaceutical excipients and additives. These include, but are not limited to, gelatin, natural sugars such as raw sugar or lactose, lecithin, pectin, starches (for example corn starch or amylose), dextran, polyvinyl pyrrolidone, polyvinyl acetate, gum arabic, alginic acid, tylose, talcum, lycopodium, silica gel (for example colloidal), cellulose, cellulose derivatives (for example cellulose ethers in which the cellulose hydroxy groups are partially etherified with lower saturated aliphatic alcohols and/or lower saturated, aliphatic oxyalcohols, for example methyl oxypropyl cellulose, methyl cellulose, hydroxypropyl methyl cellulose, hydroxypropyl methyl cellulose phthalate), fatty acids as well as magnesium, calcium or aluminum salts of fatty acids with 12 to 22 carbon atoms, in particular saturated (for example stearates), emulsifiers, oils and fats, in particular vegetable (for example, peanut oil, castor oil, olive oil, sesame oil, cottonseed oil, corn oil, wheat germ oil, sunflower seed oil, cod liver oil, in each case also optionally hydrated); glycerol esters and polyglycerol esters of saturated fatty acids $C_{12}H_{24}O_2$ to $C_{18}H_{36}O_2$ and their mixtures, it being possible for the glycerol hydroxy groups to be totally or also only partly esterified (for example mono-, di- and triglycerides); pharmaceutically acceptable mono- or multivalent alcohols and polyglycols such as polyethylene glycol and derivatives thereof, esters of aliphatic saturated or unsaturated fafty acids (2 to 22 carbon atoms, in particular 10–18 carbon atoms) with monovalent aliphatic alcohols (1 to 20 carbon atoms) or multivalent alcohols such as glycols, glycerol, diethylene glycol, pentacrythritol, mannitol, sorbitol, mannitol and the like, which may optionally also be etherified, esters of citric acid with primary alcohols, acetic acid, urea, benzyl benzoate, dioxolanes, glyceroformals, tetrahydrofurfuryl alcohol, polyglycol ethers with $C_1$–$C_{12}$-alcohols, dimethylacetamide, lactamides, lactates, ethylcarbonates, silicones (in particular medium-viscous polydimethyl siloxanes), calcium carbonate, sodium carbonate, calcium phosphate, sodium phosphate, magnesium carbonate and the like.

Other auxiliary substances that may be used are those which cause disintegration (so-called disintegrants), such as: cross-linked polyvinyl pyrrolidone, sodium carboxymethyl starch, sodium carboxymethyl cellulose or microcrystalline cellulose. Conventional coating substances may also be used to produce the oral dosage form. Those that may for example be considered are: polymerizates as well as copolymerizates of acrylic acid and/or methacrylic acid and/or their esters; copolymerizates of acrylic and methacrylic acid esters with a lower ammonium group content (for example EudragitR RS), copolymerizates of acrylic and methacrylic acid esters and trimethyl ammonium methacrylate (for example EudragitR RL); polyvinyl acetate; fats, oils, waxes, fatty alcohols; hydroxypropyl methyl cellulose phthalate or acetate succinate; cellulose acetate phthalate, starch acetate phthalate as well as polyvinyl acetate phthalate, carboxy methyl cellulose; methyl cellulose phthalate, methyl cellulose succinate, -phthalate succinate as well as methyl cellulose phthalic acid half ester; zein; ethyl cellulose as well as ethyl cellulose succinate; shellac, gluten; ethylcarboxyethyl cellulose; ethacrylate-maleic acid anhydride copolymer; maleic acid anhydride-vinyl methyl ether copolymer; styrol-maleic acid copolymerizate; 2-ethyl-hexyl-acrylate maleic acid anhydride; crotonic acid-vinyl acetate copolymer; glutaminic acid/glutamic acid ester copolymer; carboxymethylethylcellulose glycerol monooctanoate; cellulose acetate succinate; polyarginine.

Plasticizing agents that may be considered as coating substances are: Citric and tartaric acid esters (acetyl-triethyl citrate, acetyl tributyl-, tributyl-, triethyl-citrate); glycerol and glycerol esters (glycerol diacetate, -triacetate, acetylated monoglycerides, castor oil); phthalic acid esters (dibutyl-, diamyl-, diethyl-, dimethyl-, dipropyl-phthalate), di-(2-methoxy- or 2-ethoxyethyl)-phthalate, ethylphthalyl glycolate, butylphthalylethyl glycolate and butylglycolate; alcohols (propylene glycol, polyethylene glycol of various chain lengths), adipates (diethyladipate, di-(2-methoxy- or 2-ethoxyethyl)-adipate; benzophenone; diethyl- and diburylsebacate, dibutylsuccinate, dibutyltartrate; diethylene glycol dipropionate; ethyleneglycol diacetate, -dibutyrate, -dipropionate; tributyl phosphate, tributyrin; polyethylene glycol sorbitan monooleate (polysorbates such as Polysorbar 50); sorbitan monooleate.

As mentioned above, the adenosine analogs may be orally administered or coadministered in a liquid dosage form. For the preparation of solutions or suspensions it is, for example, possible to use water, particularly sterile water, or physiologically acceptable organic solvents, such as alcohols (ethanol, propanol, isopropanol, 1,2-propylene glycol, polyglycols and their derivatives, fatty alcohols, partial esters of glycerol), oils (for example peanut oil, olive oil, sesame oil, almond oil, sunflower oil, soya bean oil, castor oil, bovine hoof oil), paraffins, dimethyl sulphoxide, triglycerides and the like.

In the case of drinkable solutions the following substances may be used as stabilizers or solubilizers: lower aliphatic mono- and multivalent alcohols with 2–4 carbon atoms, such as ethanol, npropanol, glycerol, polyethylene glycols with molecular weights between 200–600 (for example 1 to 40% aqueous solution), diethylene glycol monoethyl ether, 1,2-propylene glycol, organic amides, for example amides of aliphatic $C_1$–$C_6$-carboxylic acids with ammonia or primary, secondary or tertiary $C_1$–$C_4$-amines or $C_1$–$C_4$-hydroxy amines such as urea, urethane, acetamide, N-methyl acetamide, N, N-diethyl acetamide, N, N-dimethyl acetamide, lower aliphatic amines and diamines with 2–6 carbon atoms, such as ethylene diamine, hydroxyethyl theophylline, tromethamine (for example as 0.1 to 20% aqueous solution), aliphatic amino acids.

In preparing the inventive compositions, it is possible to use known and conventional solubilizers or emulsifiers. Solubilizers and emulsifiers that may for example be used are: polyvinyl pyrrolidone, sorbitan fatty acid esters such as sorbitan trioleate, phosphatides such as lecithin, acacia, tragacanth, polyoxyethylated sorbitan monooleate and other ethoxylated fatty acid esters of sorbitan, polyoxyethylated fats, polyoxyethylated oleotriglycerides, linolizated oleotriglycerides, polyethylene oxide condensation products of fatty alcohols, alkylphenols or fatty acids or also 1-methyl-3-(2-hydroxyethyl)imidazolidone-(2). In this context, polyoxyethylated means that the substances in question contain polyoxyethylene chains, the degree of polymerization of which generally lies between 2 and 40 and in particular between 10 and 20.

Polyoxyethylated substances of this kind may for example be obtained by reaction of hydroxyl group-containing compounds (for example mono- or diglycerides or unsaturated compounds such as those containing oleic acid radicals) with ethylene oxide (for example 40 Mol ethylene oxide per 1 Mol glyceride).

Examples of oleotriglycerides are olive oil, peanut oil, castor oil, sesame oil, cottonseed oil, corn oil. See also Dr. H. P. Fiedler "Lexikon der Hillsstoffe fur Pharmazie, Kostnetik und angrenzende Gebiete" 1971, pages 191–195.

It is also possible to add preservatives, stabilizers, buffer substances, flavor correcting agents, sweeteners, colorants, antioxidants and complex formers and the like. Complex formers which may be for example be considered are: chelate formers such as ethylene diamine retrascetic acid, nitrilotriacetic acid, diethylene triamine pentacetic acid and their salts.

It may optionally be necessary to stabilize the adenosine analog with physiologically acceptable bases or buffers to a pH range of approximately 6 to 9. Preference may be given to as neutral or weakly basic a pH value as possible (up to pH 8).

In some dosage forms, it may be useful to include antioxidants or preservatives. Antioxidants that may for example be used are sodium sulphite, sodium hydrogen sulphite, sodium metabisulphite, ascorbic acid, ascorbylpalmitate, -myristate, -stearate, gallic acid, gallic acid alkyl ester, butylhydroxyamisol, nordihydroguaiaretic acid, tocopherols as well as synergists (substances which bind heavy metals through complex formation, for example lecithin, ascorbic acid, phosphoric acid ethylene diamine tetracetic acid, citrates, tartrates). Addition of synergists substantially increases the antioxygenic effect of the antioxidants.

Preservatives that may for example be considered are sorbic acid, p-hydroxybenzoic acid esters (for example lower alkyl esters), benzoic acid, sodium benzoate, trichloroisobutyl alcohol, phenol, cresol, benzethonium chloride, chlorhexidine and formalin derivatives.

The various oral dosage forms can be prepared according to conventional procedures. For example, tablets can be prepared according to common tableting procedures. Capsules can be prepared according to conventional encapsulating procedures. Liquid dosage forms may be supplied as a made up vial, or may be supplied in a lyophilized state for dilution just prior to administration. Controlled release dosage forms may be prepared according to the particular dosage form being used, as is discussed in brief above.

Dosage amounts and frequency will vary according to the particular adenosine analog, oral dosage form, and individual patient characteristics. Generally speaking, determining the dosage amount and frequency for a particular adenosine analog, oral dosage form, and individual patient characteristic can be accomplished using conventional dosing studies, coupled with appropriate diagnostics. In preferable embodiments, the dosage frequency ranges from daily to monthly doses, more preferably biweekly doses. In other preferable embodiments, the dosage amount ranges from about 0.2 mg/m$^2$ to about 20 mg/m$^2$, more preferably about 3 mg/m$^2$ to about 10 mg/m$^2$.

The adenosine analogs of the present invention may be used to treat a variety of indications. These indications include hematological malignancies, solid tumors sensitive to adenosine analogs or adenosine deaminase inhibitors, ischemia, CD4+ T cell mediated diseases, autoimmune diseases mediated by adenosine or adenosine deaminase, inflammatory diseases mediated by adenosine or adenosine deaminase, stroke, myocardial infarction, and ventricular arrhythmia. Additionally, the adenosine analogs according to the invention may also be used to treat leukemia, including hairy cell leukemia, and chronic lymphocytic leukemia, chronic T-cell lymphoma, and acute myelogenous lymphoma.

It will be apparent to those skilled in the art that various modifications and variations can be made in the compositions, kits, and methods of the present invention without departing from the spirit or scope of the invention. Thus, it is intended that the present invention cover the modifications and variations of this invention provided they come within the scope of the appended claims and their equivalents. Additionally, the following examples are appended for the purpose of illustrating the claimed invention, and should not be construed so as to limit the scope of the claimed invention.

EXAMPLES

Example 1

5 mg of pentostatin are mixed with 50 ml of sterile water and 1 mg of sodium saccharide as a sweetener. The mixture is agitated for two minutes, and then charged into a cup for oral administration to a patient.

Example 2

5 mg of fludarabine monophosphate are compounded with 50 gm of polyvinyl pyrrolidone and 50 gm of talcum. This mixture is then tableted using a conventional tableting press. The resulting tablet is then coated with methacrylic acid-methacrylic acid ester copolymer to a 2 mm dried coating thickness to form a enterically c oated tablet.

Example 3

10 mg of cladribine are compounded with 100 gm of polyvinyl pyrrolidone, 100 gm of talcum, and 10 gm of sodium carboxymethyl cellulose. This mixture is then tableted using a conventional tableting press. The resulting tablet is then coated with methacrylic acid-methacrylic acid ester copolymer to a 2 mm dried coating thickness to form a enterically coated tablet.

Example 4

5 mg of pentostatin are compounded with 100 m of cimetidine, 50 gm of polyvinyl pyrrolidone, 50 gm of talcum, and 10 gm of sodium carboxymethyl cellulose. This mixture is then tableted using a conventional tableting press. The resulting tablet is then coated with methacrylic acid-methacrylic acid ester copolymer to a 2 mm dried coating thickness to form a enterically coated tablet.

Example 5

5 mg of pentostatin are mixed with 25 mg of natural gelatin, and a small of amount of red colorant. This mixture is then charged into a standard, water-soluble, pharmaceutical grade capsule. The capsule is then sealed, making it ready for use as an oral dosage form.

Example 6

10 mg of cladribine is dissolved in a 0.1N NaCl solution under agitation. To this solution is added a cationic exchange resin. The mixture is allowed to complex over several hours under gentle agitation at room temperature, using conventional complexation techniques. After the complexing is complete, the drug-resin complex is separated from the remaining liquid. The drug-resin complex is then resuspended in a conventional buffered liquid pharmaceutical vehicle suitable for oral administration.

Example 7

5 mg of fludarabine monophosphate are mixed with 50 ml of sterile water, 20 mg of lecithin, and 1 mg of sodium saccharide as a sweetener. The mixture is agitated for two minutes, and then charged into a cup for oral administration to a patient.

Example 8

The bioavailability of 2'-deoxycoformycin (dCF) after the oral administration to beagle dogs was examined. Additionally, the single dogs in the 5× and 20× ad usum rate dose groups were pretreated with the H2-blocker, cimetidine to enhance the bioavailability of dCF, which has been reported to be acid-labile. A fourth dog was administered an oral 20× dosage without cimetidine as a control. Bioavailability was determined by assessing changes in plasma adenosine deaminase (ADA) activity, according to the methods generally outlined in L. E. Rodman et al., Toxicity of Cordycepin in Combination with the Adenosine Deaminase Inhibitor 2'-Deoxycoformycin in Beagle Dogs, Toxicol. Appl. Pharmacol. 147:39–45 (1997).

Twenty-five vials of NIPENT®, each containing 10 mg of 2'-deoxycoformycin (supplied by Supergen, Inc., San Ramon Calif.), were used. The test articles were stored refrigerated until used. The control articles used for the NIPENT® dose formulations were Sterile Water for Injection, USP (Phoenix Pharmaceutical, Inc.; St. Joseph, Mo.), and sterile 100 mM sodium phosphate buffer, pH 7.4 which was a mixture of sodium phosphate monobasic monohydrous (EM Science; Gibbstown, N.J.).

The NIPENT® vials were reconstituted in either 5 mL of Sterile Water for Injection, USP, or 5 mL of 100 mM sodium phosphate buffer. The contents were mixed thoroughly to attain a solution containing 2 mg/mL of 2'-deoxycoformycin.

Four female beagle dogs were assigned to this study. Their cage size and animal care conformed to the guidelines of the *Guide for the Care and Use of Laboratory Animals* (7 th Edition; Institute of Laboratory Animal Resources, Commission on Life Sciences, National Research Council; National Academy Press, Washington, D.C. 1996), and the U.S. Department of Agriculture through the Animal Welfare Act (7 USC 2131, 1985) and Public Law 99–198. None of the dogs died during the course of this study.

On days 0 and 1 of the study, each dog received a single oral (PO) or intravenous (IV) dose of the test article, with or without pretreatment with cimetidine, an H2 blocker. Each dog was dosed according to one of the following regimens:

| Group | Animal ID | Dose | Treatment Regimen |
|---|---|---|---|
| 1 | 2092 | 1× | 0.25 mg/kg, IV, for 2 days, with cimetidine pretreatment |
| 2 | 2094 | 5× | 1.25 mg/kg, PO, for 2 days, with cimetidine pretreatment |
| 3 | 2091 | 20× | 5.0 mg/kg, PO, for 2 days, with cimetidine pretreatment |
| 4 | 2093 | 20× | 5.0 mg/kg, PO, for 2 days, without cimetidine pretreatment |

Doses were based on the body weights taken on Day-1 and were administered at approximately the same time both days. The dogs in Groups 1, 2, and 3 were each given approximately 100 mg of cimetidine (Tagamet® HB 200; Smith/Kline Beecham Consumer Healthcare, L.P., Pittsburgh, Pa.) three times daily on Days-1, 0, and 1; the second and third daily doses were administered at approximately 3 and 6 hours after the first daily dose.

Individual animal plasma adenosine deaminase activity levels are presented in Table 2 below. The levels of plasma ADA activity remained markedly suppressed (0–3% of control values) for up to 48 hours after the last oral administration in dogs administered dCF at the 20× level (5 mg/kg). There were no discernable differences in suppression of ADA activity at this level with or without prior administration of cimetidine. In the dog administered dCF at the 5× level (1.25 mg/kg), ADA activity had reached 14% of control by 48 hours after the final administration of dCF, whereas plasma ADA activity in the dog administered dCF at the 1× level (0.25 mg/kg) reached 24% of control by approximately 24 hours after the final administration.

TABLE 2

Individual Animal Plasma Adenosine Deaminase Activity

| Animal ID (Group) | Treatment | Time after dosing (hours) | Conversion of Substrate Cordycepin to Product 3'-deoxyinosine (%) | Product Formed (nmoles) | Relative Activity (% of Control)[3] |
|---|---|---|---|---|---|
| 2092 (1) | 0.25 mg/kg IV | 0 | 1.27 ± 0.21 | 2.54 | 100 |
| | | 1 | 0.00 ± 0.03 | 0.00 | 0 |
| | (1×) | 2 | 0.04 ± 0.06 | 0.08 | 3 |
| | with | 8 | 0.00 ± 0.01 | 0.00 | 0 |
| | cimetidine | 24 | 0.00 ± 0.03 | 0.00 | 0 |
| | pre-treatment | 48 | 0.31 ± 0.12 | 0.62 | 24 |
| | | 72 | 0.28 ± 0.01 | 0.56 | 22 |
| 2094 (2) | 1.25 mg/kg PO | 0 | 2.33 ± 0.18 | 4.66 | 100 |
| | | 1 | 0.00 ± 0.06 | 0.00 | 0 |
| | (5×) | 2 | 0.06 ± 0.10 | 0.12 | 3 |
| | with | 8 | 0.02 ± 0.02 | 0.04 | 1 |
| | cimetidine | 24 | 0.03 ± 0.00 | 0.06 | 1 |
| | pre-treatment | 48 | 0.01 ± 0.06 | 0.02 | 0 |
| | | 72 | 0.33 ± 0.12 | 0.66 | 14 |
| 2091 (3) | 5.0 mg/kg PO | 0 | 1.54 ± 0.08 | 3.08 | 100 |
| | | 1 | 0.00 ± 0.05 | 0.00 | 0 |
| | (20×) | 2 | 0.02 ± 0.06 | 0.04 | 1 |
| | with | 8 | 0.01 ± 0.04 | 0.02 | 1 |
| | cimetidine | 24 | 0.05 ± 0.04 | 0.10 | 3 |
| | pre-treatment | 48 | 0.01 ± 0.05 | 0.02 | 1 |
| | | 72 | 0.00 ± 0.03 | 0.00 | 0 |
| 2093 (4) | 5.0 mg/kg PO | 0 | 3.14 ± 0.44 | 6.28 | 100 |
| | | 1 | 0.00 ± 0.04 | 0.00 | 0 |
| | (20×) | 2 | 0.00 ± 0.02 | 0.00 | 0 |
| | without | 8 | 0.00 ± 0.08 | 0.00 | 0 |
| | cimetidine | 24 | 0.07 ± 0.05 | 0.14 | 2 |
| | pre-treatment | 48 | 0.03 ± 0.07 | 0.06 | 1 |
| | | 72 | 0.04 ± 0.05 | 0.08 | 1 |

[3]Analytical control value = 3.2 ± 0.5

What is claimed is:

1. A method for treating a patient having a disease, comprising:
   orally administering to the patient a pharmacoutically-effective amount of a composition which is adapted for oral administration and comprises
   an acid-labile 2'-deoxyadenosine analog which chemically decomposes In an acidic environment of the stomach, and
   one or more components of the composition which inhibit the 2'-deoxy adenosine analog from decomposing in the acidic environment of the stomach by isolating the adenosine analog from the acidic environment of the stomach,
   wherein
   the disease is selected from the group consisting of hematological malignanies and solid tumors; and
   the one or more components of the composition are selected from the group consisting of erodible matrix, enteric coating, solid dispersion, and ion exchange resin.

2. The method according to claim 1 wherein the 2'-deoxyadenosine analog is pentostatin.

3. The method according to claim 1 wherein the enteric coating comprises a member of the group consisting of hydroxypropyl-methylcellulose phthalate, methacrylic acid-methacrylic acid ester copolymer, polyvinyl acetate-phthalate and cellulose acetate phthalate.

4. The method according to claim 1 wherein the solid dispersion comprises a carrier selected from the group consisting of polyethylene glycol, polyvlnylpyrrolldone, hydroxypropylmethyl cellulose, phosphatidylcholine, polyoxyethylone hydrogenated castor oil, hydroxypropylmethylcellulose phthalate, carboxymethylethylcellulose, hydroxypropylmethylcellulose, ethyl cellulose and stearic acid.

5. The method according to claim 1 wherein the composition is in a form selected from the group consisting of pill, capsule, liquid, lozenge, and tablet.

6. The method according to claim 1 wherein the hematoloalcal maligances include leukemia.

7. The method according to claim 6 wherein the leukemia is selected from the group consisting of hairy cell leukemia, chronic lymphocytic leukemia, chronic T-cell lymphoma, acute myelogenous lymphoma, hairy cell leukemia, and chronic lyrnphocytic leukemia.

8. The method according to claim 1 wherein the orally administering the composition to the patient includes orally administering the composition in a controlled-release mechanism.

9. The method according to claim 8 wherein the controlled-release mechanism is selected from the group consisting of a reservoir system with a rate-controlling membrane, reservoir system without a rate-controlling membrane, monollthic system, and osmotic pump.

10. The method according to claim 8 wherein the controlled-release mechanism is selected from the group consisting of SODAS, INDAS, IPDAS, MODAS, EFVAS, PRODAS, and DUREDAS.

11. The method according to claim 8 wherein the controlled-release mechanism is selected from the group consisting of a rate-preprogrammed drug delivery system, an activation-modulated drug delivery system, a feedback-regulated drug delivery system, and a site-targeting drug delivery system.

* * * * *